United States Patent
Husbyn et al.

[11] Patent Number: 5,948,759
[45] Date of Patent: Sep. 7, 1999

[54] FACTOR VII FRAGMENT 82-128 AND ITS USE IN BLOOD-CLOTTING DISORDERS

[75] Inventors: Mette Husbyn; Peter Fischer; Lars Orning, all of Oslo, Norway

[73] Assignee: Nycomed Imaging AS, Oslo, Norway

[21] Appl. No.: 08/849,248

[22] PCT Filed: Dec. 15, 1995

[86] PCT No.: PCT/GB95/02946

§ 371 Date: Aug. 27, 1997

§ 102(e) Date: Aug. 27, 1997

[87] PCT Pub. No.: WO96/18654

PCT Pub. Date: Jun. 20, 1996

[30] Foreign Application Priority Data

Dec. 15, 1994 [GB] United Kingdom ............. 9425381

[51] Int. Cl.[6] .................... A61K 38/17; A61K 38/36; C07K 14/435; C07K 14/745
[52] U.S. Cl. ................. 514/12; 514/822; 530/300; 530/324; 530/384; 536/23.5
[58] Field of Search ............ 424/94.63, 94.64; 435/69.2, 212, 219, 226; 514/12, 2, 822; 530/300, 324, 384; 536/23.5

[56] References Cited

FOREIGN PATENT DOCUMENTS

| | | |
|---|---|---|
| 90 03390 | 4/1990 | WIPO . |
| 91 07432 | 5/1991 | WIPO . |
| 95 00541 | 1/1995 | WIPO . |
| 95 00847 | 1/1995 | WIPO . |

OTHER PUBLICATIONS

Kazama et al., *J. Biol. Chem.*, vol. 268, No. 22, Aug. 5, 1993, pp. 16231–16240.

*Primary Examiner*—Dian C. Jacobson
*Attorney, Agent, or Firm*—Bacon & Thomas

[57] ABSTRACT

The present invention relates to peptide of the amino acid sequence of formula (I):

```
 82              85                      90
Glu Thr His Lys Asp Asp Gln Leu Ile
                 95                     100
Cys Val Asn Glu Asn Gly Gly Cys Glu Gln
                105                     110
Tyr Cys Ser Asp His Thr Gly Thr Lys Arg
                115                     120
Ser Cys Arg Cys His Glu Gly Tyr Ser Leu
                125         128
Leu Ala Asp Gly Val Ser Cys Thr (SEQ ID NO. 1)
``` and functional equivalents thereof in which amino acids in the above stated sequence are modified or absent and wherein at least one of the cysteine residues may be blocked or replaced and wherein any cysteine residues which remain unblocked or unreplaced may be present in a disulphide bonded state. The invention also includes slats and derivatives of said peptides. The peptides and their salts and derivatives are useful in the treatment of blood clotting disorders.

14 Claims, No Drawings

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 47 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

```
Glu Thr His Lys Asp Asp Gln Leu Ile Cys Val Asn Glu Asn Gly
 1               5                  10                  15

Cys Glu Gln Tyr Cys Ser Asp His Thr Gly Thr Lys Arg Ser Cys
                20                  25                  30

Cys His Glu Gly Tyr Ser Leu Leu Ala Asp Gly Val Ser Cys Thr
                35                  40                  45
```

(2) INFORMATION FOR SEQ ID NO: 2:

(i) SEQUENCE CHARACTERISTICS:
      (A) LENGTH: 47 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION:10
      (D) OTHER INFORMATION:/product= "10"
          /note= "Xaa represents Abu"

(ix) FEATURE:
      (A) NAME/KEY: Modified-site
      (B) LOCATION:17
      (D) OTHER INFORMATION:/product= "17"
          /note= "Xaa represents Abu"

(ix) FEATURE:
      (A) NAME/KEY: Modified-site
      (B) LOCATION:21
      (D) OTHER INFORMATION:/product= "21"
          /note= "Xaa represents Abu"

(ix) FEATURE:

```
            (A) NAME/KEY: Modified-site
            (B) LOCATION:31
            (D) OTHER INFORMATION:/product= "31"
                /note= "Xaa represents Abu"

(ix) FEATURE:
            (A) NAME/KEY: Modified-site
            (B) LOCATION:33
            (D) OTHER INFORMATION:/product= "33"
                /note= "Xaa represents Abu"

(ix) FEATURE:
            (A) NAME/KEY: Modified-site
            (B) LOCATION:46
            (D) OTHER INFORMATION:/product= "46"
                /note= "Xaa represents Abu"

(xi) SEQUENCE DESCRIPTION: SEQ ID NO: 2:

Glu Thr His Lys Asp Asp Gln Leu Ile Xaa Val Asn Glu Asn Gly
1               5                   10                  15

Xaa Glu Gln Tyr Xaa Ser Asp His Thr Gly Thr Lys Arg Ser Xaa
                20                  25                  30

Xaa His Glu Gly Tyr Ser Leu Leu Ala Asp Gly Val Ser Xaa Thr
                35                  40                  45

(2) INFORMATION FOR SEQ ID NO: 3:

(i) SEQUENCE CHARACTERISTICS:
            (A) LENGTH: 47 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION:17
            (D) OTHER INFORMATION:/product= "17"
                /note= "Xaa represents Abu"

(ix) FEATURE:
            (A) NAME/KEY: Modified-site
            (B) LOCATION:31
            (D) OTHER INFORMATION:/product= "31"
                /note= "Xaa represents Abu"

(ix) FEATURE:
            (A) NAME/KEY: Modified-site
            (B) LOCATION:33
            (D) OTHER INFORMATION:/product= "33"
                /note= "Xaa represents Abu"

(ix) FEATURE:
            (A) NAME/KEY: Modified-site
            (B) LOCATION:46
            (D) OTHER INFORMATION:/product= "46"
                /note= "Xaa represents Abu"

(xi) SEQUENCE DESCRIPTION: SEQ ID NO: 3:

Glu Thr His Lys Asp Asp Gln Leu Ile Cys Val Asn Glu Asn Gly
1               5                   10                  15

Xaa Glu Gln Tyr Cys Ser Asp His Thr Gly Thr Lys Arg Ser Xaa
                20                  25                  30

Xaa His Glu Gly Tyr Ser Leu Leu Ala Asp Gly Val Ser Xaa Thr
                35                  40                  45

(2) INFORMATION FOR SEQ ID NO: 4:

(i) SEQUENCE CHARACTERISTICS:
            (A) LENGTH: 47 amino acids
            (B) TYPE: amino acid
```

```
            (C) STRANDEDNESS: single
            (D) TOPOLOGY: linear (ii) MOLECULE TYPE: peptide (ix) FEATURE:
            (A) NAME/KEY: Modified-site
            (B) LOCATION:10
            (D) OTHER INFORMATION:/product= "10"
                /note= "Xaa represents Abu"

(ix) FEATURE:
            (A) NAME/KEY: Modified-site
            (B) LOCATION:17
            (D) OTHER INFORMATION:/product= "17"
                /note= "Xaa represents Abu"

(ix) FEATURE:
            (A) NAME/KEY: Modified-site
            (B) LOCATION:21
            (D) OTHER INFORMATION:/product= "21"
                /note= "Xaa represents Abu"

(ix) FEATURE:
            (A) NAME/KEY: Modified-site
            (B) LOCATION:31
            (D) OTHER INFORMATION:/product= "31"
                /note= "Xaa represents Abu"

(xi) SEQUENCE DESCRIPTION: SEQ ID NO: 4:

Glu Thr His Lys Asp Asp Gln Leu Ile Xaa Val Asn Glu Asn Gly
1               5                   10                  15

Xaa Glu Gln Tyr Xaa Ser Asp His Thr Gly Thr Lys Arg Ser Xaa
            20                  25                  30

Cys His Glu Gly Tyr Ser Leu Leu Ala Asp Gly Val Ser Cys Thr
            35                  40                  45

(2) INFORMATION FOR SEQ ID NO: 5:

(i) SEQUENCE CHARACTERISTICS:
            (A) LENGTH: 47 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION:10
            (D) OTHER INFORMATION:/product= "10"
                /note= "Xaa represents Abu"

(ix) FEATURE:
            (A) NAME/KEY: Modified-site
            (B) LOCATION:21
            (D) OTHER INFORMATION:/product= "21"
                /note= "Xaa represents Abu"

(ix) FEATURE:
            (A) NAME/KEY: Modified-site
            (B) LOCATION:33
            (D) OTHER INFORMATION:/product= "33"
                /note= "Xaa represents Abu"

(ix) FEATURE:
            (A) NAME/KEY: Modified-site
            (B) LOCATION:46
            (D) OTHER INFORMATION:/product= "46"
                /note= "Xaa represents Abu"

(xi) SEQUENCE DESCRIPTION: SEQ ID NO: 5:
```

```
Glu Thr His Lys Asp Asp Gln Leu Ile Xaa Val Asn Glu Asn Gly
1               5                   10                  15

Cys Glu Gln Tyr Xaa Ser Asp His Thr Gly Thr Lys Arg Ser Cys
                20              25              30

Xaa His Glu Gly Tyr Ser Leu Leu Ala Asp Gly Val Ser Xaa Thr
            35              40              45
```

(2) INFORMATION FOR SEQ ID NO: 6:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "recombinant DNA"

(xi) SEQUENCE DESCRIPTION: SEQ ID NO: 6:

```
GAGACGCACA AGGATGACCA GCTGATCTGT GTGAACGAGA ACGGCGGCTG TGAGCAGTAC        60

TGCAGTGACC ACACGGGCAC CAAGCGCTCC TGTCGGTGCC ACGAGGGGTA CTCTCTGCTG       120

GCAGACGGGG TGTCCTGCAC A                                                 141
```

FACTOR VII FRAGMENT 82-128 AND ITS USE IN BLOOD-CLOTTING DISORDERS

The present invention is concerned with peptide reagents and compositions thereof which reduce blood clot formation.

Blood clotting relies upon a series or cascade of activating reactions to produce the ultimate fibrin clot. The cascade leading to fibrin formation may be triggered initially in two different ways—by contact with abnormal surfaces (the "intrinsic pathway") or by traumatization of blood vessels which causes secretion of the lipoprotein known as "tissue factor" or TF (the "extrinsic pathway"). The present invention is primarily concerned with the extrinsic blood clotting pathway.

Coagulation factor VII(FVII) is a plasma glycoprotein of $M_r$=50,000 consisting of a single polypeptide chain with 406 amino acid residues (F. S. Hagen et al., Proc. Natl. Acad. Sci. USA, 1986, 83: 2412–2416; P. J. O'Hara et al., Proc. Natl. Acad. Sci. USA, 1987, 84: 5158–5162). The zymogen form is converted to the fully enzymatically active form $FVII_a$, by factor X and other coagulation proteases through hydrolysis of a single peptide bond $Arg^{152}$-$Ile^{153}$. This results in formation of an enzyme with two polypeptide chains which are held together by a single disulphide bond. The light chain of 152 amino acid residues contains at its amino terminal part the γ-carboxy-glutamic acid (Gla) domain, followed by two epidermal growth factor-like domains (EGF-1 and EGF-2). The heavy chain consists of 254 residues and contains the serine protease catalytic domain. The function of $FVII_a$ is activation of factor X (FX) by complexation with tissue factor (TF) in the presence of $Ca^{2+}$ on a phospholipid membrane surface. Activation of FX to $FX_a$ leads to formation of blood clots by the extrinsic pathway. Additionally, the complex $FVII_a$/TF can activate factor IX to factor $IX_a$ and lead to clotting through the intrinsic pathway.

Activation of the extrinsic pathway for blood clot formation is the primary event leading to fibrin formation and is thus of prime importance in the pathogenesis of arteriosclerotic lesions and in reocclusion and restenosis following endarterectomy. One way of providing potential therapeutic agents capable of preventing the primary event in blood clot formation through the extrinsic pathway would thus be to identify peptides derived from the primary structure of FVII which are capable of inhibiting the complex formation between FVII, TF and FX, which is necessary for FX activation.

Comparatively little is known about the mechanism and sites of interaction of FVII with TF and FX at the molecular level. Nevertheless, a number of FVII-derived peptides have been identified which possess some inhibitory activity with respect to FX activation and which are not inhibitors of the enzymatic activity of $FVII_a$. Peptides corresponding to sequence portions between the Gla and EGF-1 domains as well as from the catalytic domain, were disclosed in WO 9107432 (Board of Regents, The University of Texas System). A particular peptide from the EGF-2 domain, as well as another peptide from the heavy chain were disclosed in WO 9003390 (Corvas, Inc.). Furthermore, we have disclosed in a co-pending application (PCT/GB94/01315) certain small peptides from the EGF-1 and mainly from the EGF-2 domains. In general the literature suggests that the Gla domain, EGF-1 domain and certain parts of the heavy chain are important in the recognition of FX and TF by FVII (P. Wildgoose et al., Proc. Natl. Acad. Sci. USA, 1990, 87: 7290–7294; W. Ruf et al., J. Biol. Chem., 1991, 266: 15719–15725; A. Kumar et al., Eur. J. Biochem., 1993, 217: 509–518; S. Higashi et al., J. Biol. Chem., 1994, 269: 18891–19989).

We have investigated the EGF-2 domain of FVII and its role in protein-protein interactions involving FVII. The arrangement of the three disulphide bonds present in the EGF-2 domain of FVII is believed to follow a general pattern for proteins containing EGF-like domains and for epidermal growth factor itself (H. Gregory, Nature, 1975, 257: 325–327). For the FVII EGF-2 domain this corresponds to the following half-cysteine pairs: $Cys^{91}$–$Cys^{102}$, $Cys^{98}$–$Cys^{112}$ and $Cys^{114}$–$Cys^{127}$. We have prepared various peptide analogues incorporating the EGF-2 domain of FVII by chemical synthesis and found that a fragment from $Glu^{82}$ to $Thr^{128}$ and variants of this have surprising activity in blocking the interaction of FVII with TF in FX activation.

The fragment FVII 82–128 can be written in full as follows:

```
82              85                      90
Glu Thr His Lys Asp Asp Gln Leu Ile
                95                     100
Cys Val Asn Glu Asn Gly Gly Cys Glu Gln
               105                     110
Tyr Cys Ser Asp His Thr Gly Thr Lys Arg
               115                     120
Ser Cys Arg Cys His Glu Gly Tyr Ser Leu
               125         128
Leu Ala Asp Gly Val Ser Cys Thr [SEQ ID NO. 1]
```

We have found that even when the three disulphide bonds of the native structure are absent in one of our synthetic EGF-2 domain peptides (by providing 2-aminobutyric acid (Abu) replacements for the Cys residues to produce a linear peptide) a potent inhibitor of FX activation is obtained.

The inhibition of FVII function by a number of synthetic peptides including the above linear peptide was determined in a two-stage chromogenic assay as described (A. Kumar et al., 1991, J. Biol. Chem., 266@ 915–921). This consisted of incubation of peptide dilutions with mixtures of TF and FX, followed by addition of the test peptide and determination of the rate of FVII-induced FX activation by kinetic measurement of FX amidolysis of a chromogenic substrate. The concentrations of peptides required to inhibit the rate of FX activation by 50% ($IC_{50}$) was determined, including appropriate controls (buffer control, non-related synthetic peptide) and the results are shown in the following table.

| Peptide position in factor VII | $IC_{50}$ (mM) |
|---|---|
| Ac-$Trp^{41}$-. . . -$Asp^{48}$-$NH_2$ | 0.29 |
| H-$Asn^{95}$-. . . -$Asp^{104}$-OH | 0.62 |
| Ac-$Ser^{103}$-. . . -$Ser^{111}$-$NH_2$ | >1 |

| Peptide position in factor VII | IC$_{50}$ (mM) |
|---|---|
| Ac-Asp$^{196}$-. . . -Ala$^{206}$-NH$_2$ | >1 |
| disulphide-cyclo-[H-Cys$^{72}$. . . -Cys$^{81}$-OH] | 0.77 |
| disulphide-cyclo-[H-Cys$^{91}$. . . -Cys$^{102}$-OH] | 0.70 |
| disulphide-cyclo-[H-Cys$^{114}$. . . -Cys$^{127}$-OH] | >1 |
| Abu$^{91,98,102,112,114,127}$-[Glu$^{82}$-. . . -Thr$^{128}$] | 0.001 |

[SEQ ID NO. 1]

The surprisingly high inhibitory potency of the above linear EGF-2 domain peptide, when compared to smaller peptides from the EGF-2 domain and other peptides previously proposed as use Arg Cys His Glu Gly Tyr Ser, Arg Cys His Glu Gly Tyr Ser Leu, Arg Cys His Glu Gly Tyr Ser Leu Leu, Arg Cys His Glu Gly Tyr Ser Leu Leu Ala, Arg Cys His Glu Gly Tyr Ser Leu Leu Ala Asp, Arg Cys His Glu Gly Tyr Ser Leu Leu Ala Asp Gly, Arg Cys His Glu Gly Tyr Ser Leu Leu Ala Asp Gly Val, Arg Cys His Glu Gly Tyr Ser Leu Leu Ala Asp Gly Val Ser, Arg Cys His Glu Gly Tyr Ser Leu Leu Ala Asp Gly Val Ser Cys and Arg Cys His Glu Gly Tyr Ser Leu Leu Ala Asp Gly Val Ser Cys Thr.

Particularly important modifications of the FVII 82-128 sequence are those in which one or more of the cysteine residues are replaced, so as to eliminate disulphide bonding at that point. The SH groups of the cysteine residues may thus be blocked, eg. by alkylation by optionally substituted $C_{1-5}$ alkyl groups or $C_{6-12}$ aralkyl groups such as tert.butyl, carboxymethyl, benzyl, acetamidomethyl, or pyridylethyl groups. Alternatively, the cysteine residue may be replaced by a different amino acid, preferably 2-aminobutyric acid (Abu), glycine, alanine or serine.

In general, if such modification is effected, preferably one, two or three of the pairs of naturally linked cysteine residues are blocked or replaced. The fully linearised derivatives in which all six cysteines are blocked or replaced are especially preferred, notably that with Abu in place of each cysteine.

A number of conservative amino acid substitutions are recognised in the art as having little or no functional effect, notably Ser for Thr, Ile for Leu and Lys for Arg. Such modifications are also included.

The terminal amino group may be 'capped', that is blocked by an inert group such as an acyl group, eg. a $C_{1-5}$ alkanoyl group, for example acetyl. The terminal carboxyl group may also be capped, for example by formation of carbamoyl group, eg. $CONH_2$, or an ester group, eg. a $C_{1-5}$ alkoxycarbonyl group.

Salts of the peptides include physiologically acceptable acid addition salts such as the hydrochloride.

The present invention also provides pharmaceutical compositions containing one or more of the peptides of the invention or salts thereof.

The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the peptide of formula (I) or salt thereof.

As indicated above, one aspect of the invention provides peptides (including the analogues or salts thereof) according to the invention for use in the treatment or prevention of blood clotting disorders or problems. Blood clotting disorders include thrombosis (particularly vascular thrombosis or deep vein thrombosis), acute myocardial infarction, restenosis, reclosure, angina, cerebrovascular disease, peripheral arterial occlusive disease, hypercoagulability and pulmonary embolism. The peptides according to the invention can also be used to prevent occurrence of blood clotting problems caused by, for example, injury to blood vessels during thrombolytic therapy, grafting surgery, vessel patency restoration etc. Blood clotting disorders may be triggered by sepsis due to production of TNF-$\alpha$ or IL-1.

In a still further aspect, the present invention also provides a method of treatment of blood disorders in the mammalian, preferably human, animal body, said method comprising administering to said body one or more peptides of formula (I) or analogues or salts thereof. Prophylactic methods of treatment are also provided, whereby a peptide according to the invention is administered to a patient to prevent or reduce the occurrence of possible blood clotting problems, for example during surgery or other invasive techniques. The peptide will of course normally be administered in the form of a pharmaceutically acceptable composition.

In another aspect, the present invention provides a process for the preparation of peptides which comprise the sequence of formula (I) or are derived therefrom, or analogues or salts thereof.

The peptides of the present invention can be prepared by methods known in the art. Typically, the desired sequences are assembled by solid-phase peptide synthesis. Standard procedures for the synthesis strategy employed for the examples of this invention are described in E. Atherton & R. C. Sheppard, *Solid phase peptide synthesis: a practical approach,* 1989, IRL Press, Oxford. For example, a synthesis resin derivatised with an acid-labile linker group is first esterified with a protected form of the C-terminal amino acid. The amino-protecting group is then removed and the second amino acid in the sequence is coupled using a suitable condensation reagent. Amino acids with semi-permanent amino protecting groups and permanent protecting groups for functional side chains are employed. Amino-deprotection and coupling cycles are then repeated in alternating steps until the sequence of interest is assembled. Finally the permanent side-chain protecting groups are removed and the peptide is cleaved from the synthesis resin usually simultaneously through treatment with a suitable acidic reagent. Alternatively, the peptides can be synthesised through solution peptide synthesis, either in a step-wise manner from the carboxyl terminus and/or through the application of segment condensation methods, either employing comprehensive (see e.g. Y. Nishiuchi et al., (1992) in 'Peptides: Chemistry and Biology', J. A. Smith and J. E. Rivier (eds.), pp. 911–913, ESCOM, Leiden) or minimal protection/ ligation (see e.g. P. E. Dawson et al., Science, 1994, 266: 776–779) strategies. Combined solution—solid phase segment condensation approaches can also be applied (see e.g. H. Benz, Synthesis, 1994, 337–358).

Generally the reactive groups present (for example amino, thiol and/or carboxyl) will be protected during overall synthesis as indicated above. The final step in the synthesis will thus be the deprotection of a protected derivative of the peptide of the invention.

A wide choice of protecting groups for amino- acids are known and are exemplified in Schröder, E., and Lübke, K., The Peptides, Vols. 1 and 2, Academic Press, New York and London, 1965 and 1966; Pettit, G. R., Synthetic Peptides, Vols. 1–4, Van Nostrand, Reinhold, N.Y. 1970, 1971, 1975 and 1976; Houben-Weyl, Methoden der Organischen Chemie, Synthese von Peptiden, Band 15, Georg Thieme Verlag, Stuttgart 1974; Amino Acids, Peptides and Proteins, Vol.4–8, The Chemical Society, London 1972, 1974, 1975 and 1976; Peptides, Synthesis-physical data 1–6, Wolfgang Voelter, Eric Schmidt-Siegman, Georg Thieme Verlage Stuttgart, NY, 1983; The Peptides, Analysis, synthesis, biology 1–7, Ed: Erhard Gross, Johannes Meienhofer, Academic Press, NY, San Fransisco, London; Solid phase peptide synthesis 2nd ed., John M. Stewart, Janis D. Young, Pierce Chemical Company.

Thus, for example amine protecting groups which may be employed include protecting groups such as carbobenzoxy (hereinafter also designated Z) t-butoxycarbonyl (hereinafter also designated Boc) and 9-fluorenylmethoxycarbonyl (hereinafter also designated Fmoc). It will be appreciated that when the peptide is built up from the C-terminal end, an amine-protecting group will be present on the α-amino group of each new residue added and will need to be removed selectively prior to the next coupling step. One particularly useful group for such temporary amine protection is the Fmoc group which can be removed selectively by treatment with piperidine in an organic solvent.

Carboxyl protecting groups which may, for example be employed include readily cleaved ester groups such as benzyl (Bzl), p-nitrobenzyl (ONb), or t-butyl (OtBu) groups as well as the linkers on solid supports, for example p-alkoxybenzylalcohol groups linked to polystyrene.

Thiol protecting groups include p-methoxybenzyl (Mob), trityl (Trt), acetamidomethyl (Acm), t-butylsulphenyl (SBu$^t$) and 2-pyridylsulphenyl (Npys).

It will be appreciated that a wide range of other such groups exists as, for example, detailed in the above-mentioned literature references, and the use of all such groups in the hereinbefore described processes fall within the scope of the present invention.

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoro acetic acid. In general, where the pairs of cysteine residues in native FVII 82-128 remain in the SH form, they are preferably caused to interact oxidatively to form a disulphide bond.

There are two common ways of forming intramolecular disulphide bonds in synthetic peptides. In the single-step approach the reduced linear peptide is submitted directly to oxidation with an oxidant such as air or dimethylsulphoxide (J. P. Tam et al., J. Am. Chem. Soc., 1991, 113: 6657–6662). Alternatively, oxidation via disulphide exchange with reduced/oxidised glutathione or similar reagents can be employed (K. O. Johanson et al., J. Biol. Chem., 1981, 256: 445–450). The direct approach depends on the ability of the peptide in question to fold into the native state and often results in by-products with undesired disulphide pairings. The other approach is sequential in nature and involves regioselective formation of individual disulphide bonds (K. Akaji et al., Tetrahedron Lett., 1992, 33: 1073–1076). This necessitates the use of different thiol protecting groups for prospective pairs of Cys residues. The protecting groups are chosen to permit step-wise selective deprotection in the presence of pre-formed disulphide bonds. Such an approach is preferred for peptides containing multiple disulphide bonds described in this invention and has also been applied to the chemical synthesis of EGF-2 peptides from coagulation factor IX (Y. Yang et al., Protein Science, 1994, 3: 1267–1275).

The FVII EGF-2 peptides of this invention may also be produced through genetic engineering. In the first step synthetic oligonucleotides including the sequences encoding the polypeptides in question (specifically nucleotide sequences within position 459–599 according to F. S. Hagen et al., Proc. Natl. Acad. Sci. USA, 1986, 83: 2412–2416, FIG. 2) may be produced by standard methods. Alternatively, cDNA or genomic DNA digest libraries may be produced (e.g. as described in P. J. O'Hara et al., Proc. Natl. Acad. Sci. USA, 1987, 84: 5158–5162) and screened with a labelled probe specific for DNA sequences encoding the EGF-2 domain. In the second step, DNA thus produced is then cloned into suitable expression vectors, which are used to transform microorganisms (typically *Escherichia coli* bacteria or certain yeasts). Finally these microorganisms are cultured and the polypeptide products from the inserted foreign DNA are isolated from the cultures through protein chemistry methods well known in the art.

Thus, according to a further feature of the invention we provide a recombinant DNA molecule comprising an expression vector containing DNA according to the sequence:

GAG ACG CAC AAG GAT GAC CAG CTG ATC [SEQ ID No. 6]

TGT GTG AAC GAG AAC GGC GGC TGT GAG

CAG TAC TGC AGT GAC CAC ACG GGC ACC

AAG CGC TCC TGT CGG TGC CAC GAG GGG

TAC TCT CTG CTG GCA GAC GGG GTG TCC

TGC ACA and modifications thereof coding for peptides according to the invention.

The following Examples are given by way of illustration only:

EXAMPLE 1

Abu$^{91,98,102,112,114,127}$-[FVII Glu$^{82}$-Thr$^{128}$] [SEQ ID No. 2]The peptidyl resin corresponding to the above sequence was assembled on Fmoc-Thr(Bu$^t$)-[TentaGel ACS resin] (0.1 mmol; 2-methoxy-4-alkoxybenzyl alcohol handle; from Rapp Polymere GmbH, Tübingen, Germany) using an Applied Biosystems model 433A peptide synthesiser. Fmoc-deprotection was achieved with conductivity monitoring using 20% piperidine in N,N-dimethylformamide (DMF). The washing solvent was DMF. The first 20 residues (from carboxyl terminus) were coupled with 10-fold molar excess of Fmoc-amino acids amd 2-(1H-benzotriazole-1-yl)-1,1,3,3-tetramethyluronium-hexafluorophosphate/1-hydroxybenzotriazole (HOBt)/Pr$^i_2$NEt in N-methylpyrrolidone using 75 min coupling cycles. The remaining 20 residues were assembled using double couplings (75 min each cycle). Prior to Fmoc-deprotection at each sequence position capping was carried out using a solution of acetic anhydride (4.7% v/v) /Pr$^i_2$NEt (2.2% v/v)/HOBt (0.2% w/v) in DMF. The amino acid side-chain protecting groups used were: 2,2,5,7,8-pentamethylchroman-6-sulphonyl for Arg, trityl for Asn, Gln and His, t-butyloxycarbonyl for Lys, t-butyl for Asp, Glu, Ser, Thr and Tyr. The final Fmoc-deprotected and washed (Et$_2$O) peptidyl resin was dried in vacuo. An aliquot (40 mg) was treated with a mixture containing phenol, 1,2-ethanedithiol, thioanisole, water and CF$_3$COOH (0.75:0.25:0.5:0.5:10, w/v/v/v/v) for 4 h. Resin residue was then filtered off and washed with small quantities of neat CF$_3$COOH. The combined filtrate and washings were concentrated in vacuo. The crude peptide was then obtained by trituration with Et$_2$O and collection of the precipitate by centrifugation and further washes with Et$_2$O. The dried crude product (13 mg) was fractionated by semi-preparative RP-HPLC (Vydac C$_{18}$ column, 1×25 cm; 3 mL/min, 15 to 30% MeCN in 0.1% aq CF$_3$COOH over 2 h). Appropriate peak fractions were pooled and lyophilised to afford 2.0 mg of pure peptide. Analytical RP-HPLC: $t_R$=29.4 min, purity 96% (Vydac 2l8TP54, 0.46×25 cm, 1 mL/min, 15–30% MeCN in 0.1% aq CF$_3$COOH over 40 min, λ=215 nm). ES-MS: [M]= 5056.1±0.35, C$_{213}$H$_{337}$N$_{65}$O$_{78}$=5056.42. N-Terminal sequence analysis (ABI gas-phase sequencer) over the first 6 residues confirmed the presence of the desired peptide. Amino acid analysis: Asx 5.94(6), Thr 3.98(4), Ser 4.09(4), Glx 5.84(6), Gly 5.03(5), Ala 1.03(1), Val 1.99 (2), Ile 0.96(1), Leu 3.03(3), Tyr 2.02(2), His 2.97(3), Lys 2.00(2), Arg 2.02(2), Abu 6.10 (6).

EXAMPLE 2

Disulphide-cyclo [Cys$^{91}$–Cys$^{102}$]-Abu$^{98,112,114,127}$-[FVII Glu$^{82}$-Thr$^{128}$] [SEQ ID No. 3]

The peptidyl resin corresponding to the sequence Abu$^{98,112,114,127}$-[FVII Glu$^{82}$-Thr$^{128}$] was assembled in a similar fashion to the corresponding peptidyl resin of Example 1 with the exception that Cys$^{91}$ and Cys$^{102}$ were introduced as the Fmoc-Cys(SBu$^t$)-OH derivatives. The complete peptidyl resin was worked up and an aliquot (80 mg dry weight) treated with the same acidolysis reagent as in Example 1. After precipitation from Et$_2$O, the product was dissolved in 0.1% aq CF$_3$COOH with the aid of ultrasonication and was then lyophilised to yield 16.2 mg white solid material. This was redissolved in 0.1% aq CF$_3$COOH (4 mL), filtered and applied to an RP-HPLC column (Vydac 218TP1022, 2.2×25 cm). The column was developed at 5 mL/min with a gradient of 20 to 35% MeCN in 0.1% aq CF$_3$COOH over 2 h. Appropriate peak fractions were pooled and lyophilised to afford pure Cys$^{91,102}$ (SBu$^t$)-protected material. Analytical RP-HPLC: $t_R$=24.5 min, purity 97% (Vydac 218TP54, 0.46×25 cm, 1 mL/min, 20–35% MeCN in 0.1 aq CF$_3$COOH over 40 min, λ=215 nm).

This material was dissolved in a mixture of 2,2,2-trifluoroethanol and water (95:5, v/v; 2 mL) and tri-n-butylphosphine (2 drops) was added. The mixture was shaken for 1 h and was then evaporated in vacuo. The residue was precipitated from Et$_2$O, collected by centrifugation and further washed with Et$_2$O in a similar fashion. The dried reduced material was dissolved in a mixture of CF$_3$COOH and dimethylsulphoxide (95:5, v/v, 2 mL) and oxidation was allowed to proceed for 90 min. CF$_3$COOH was then removed from the mixture by rotary evaporation under water-pump vacuum. The residual solution was diluted with an equal volume of water and was applied directly to an RP-HPLC column (Vydac 218TP1022, 2.2×25 cm). The column was developed at 5 mL/min with a gradient of 20 to 30% MeCN in 0.1% aq CF$_3$COOH over 2 h. Appropriate peak fractions corresponding to the disulphide Cys$^{91,102}$ oxidised material were pooled and lyophilised to provide the title compound. Analytical RP-HPLC: $t_R$=13.3 min, purity 95% (Vydac 218TP54, 0.46×25 cm, 1 mL/min, 20–35% MeCN in 0.1% aq CF$_3$COOH over 40 min, λ=215 nm). ES-MS: [M]=5089.5±0.62, C$_{211}$H$_{331}$N$_{65}$O$_{78}$S$_2$= 5090.44. Amino acid analysis: Asx 5.80(6), Thr 3.85(4), Ser 4.40(4), Glx 5.70 (6), Gly 5.11(5), Cys 1.79(2), Ala 1.00(1), Val 2.06(2), Ile 0.85 (1), Leu 3.04 (3), Tyr 1.96 (2), His 2.92(3), Lys 1.87(2), Arg 2.01 (2), Abu 4.63(4).

EXAMPLE 3

Disulphide-cyclo [Cys$^{114}$–Cys$^{127}$]-Abu$^{91,98,102,112}$,-[FVII Glu$^{82}$-Thr$^{128}$] [SEQ ID No. 4]

The peptidyl resin corresponding to the sequence Abu$^{91,98,102,112}$,-[FVII Glu$^{82}$-Thr$^{128}$] was assembled in a similar fashion to the corresponding peptidyl resin of Example 1 with the exception that Cys$^{114}$ and Cys$^{127}$ were introduced as the Fmoc-Cys(SBu$^t$)-OH derivatives. The complete peptidyl resin was worked up and treated with the same acidolysis reagent as in Example 1. After precipitation from Et$_2$O, the product was dissolved in 0.1% aq CF$_3$COOH and was then lyophilised. This material was used directiy in the next step. Analytical RP-HPLC: $t_R$=28.3 min, major peak (Vydac 218TP54, 0.46×25 cm, 1 mL/min, 20–35% MeCN in 0.1% CF$_3$COOH over 40 min, λ=215 nm).

The Cys$^{114,127}$(SBu$^t$)-protected material was resuspended in H$_2$O. Concentrated aq ammonia solution (2 drops) was then added to bring the peptide material into solution. Pilot experiments using this procedure demonstrated that base treatment lead to very rapid removal of the t-butylsulphenyl protecting groups, as well as formation of the desired disulphide bond. The soluuon was then filtered and applied to an RP-HPLC column (Vydac 218TP1022, 2.2×25 cm). The column was developed at 5 mL.min with a gradient of 20 to 35% MeCN in 0.1% aq CF$_3$COOH over 2 hours. Appropriate peak fractions were pooled and lyophilised to afford pure title compound. Analytical RP-HPLC: $t_R$=30.3 min, purity 92% (Vydac 218TP54, 0.46×25 cm, 1 mL/min, 15–30% MeCN in 0.1% aq CF$_3$COOH over 40 min, λ=215 nm). ES-MS:[M]=5090.0, $C_{211}H_{331}N_{65}O_{78}S_2$=5090.44. Amino acid analysis: Asx 5.66(6), Thr 4.02(4), Ser 4.47(4), Glx 5.72(6), Gly 5.31(5), Cys 2.28(2), Ala 1.11(1), Val 1.76(2), Ile 0.97(1), Leu 3.20(3), Tyr 1.90(2), His 2.98(3), Lys 1.96(2), Arg 1.85(2), Abu 3.81(4).

EXAMPLE 4

Disulphide-cyclo [$Cys^{98}$–$Cys^{112}$]-$Abu^{91,102,114,127}$-[FVII $Glu^{82}$-$Thr^{128}$] [SEQ ID No. 5]

The peptidyl resin corresponding to the sequence $Abu^{91,102,114,127}$-[FVII $Glu^{82}$-$Thr^{128}$] was assembled in a similar fashion to the corresponding peptidyl resin of Example 1 with the exception that $Cys^{98}$ and $Cys^{112}$ were introduced as the Fmoc-Cys(Acm)-OH derivatives. The complete peptidyl resin was worked up and an aliquot treated with the same acidolysis reagent as in Example 1. After precipitation from $Et_2O$, the product was dissolved in 0.1% aq $CF_3COOH$ and was then lyophilised. The residue was redissolved in 0.1% aq $CF_3COOH$, filtered and applied to an RP-HPLC column (Vydac 2187TP1022, 2.2×25 cm). The column was developed at 5 mL/min with a gradient of 15 to 30% MeCN in 0.1% aq $CF_3COOH$ over 2 hours. Appropriate peak fractions were pooled and lyophilised to afford pure $Cys^{98,112}$(Acm)-protected material. MALDI-TOF MS: $[M+H]^+$=5235.1, $C_{217}H_{343}N_{67}O_{80}S_2$=5234.65.

Acm-deprotection was carried out as follows: The $Cys^{98,112}$(Acm)-protected material (2 mg) was dissolved in 30% aq AcOH (0.4 mL) and $Hg(OAc)_2$ (3 mg) was added. The solution was agitated at ambient temperature for 4 hours. 2-Mercaptoethanol (10 μL) was then added and the mixture was left overnight. It was then diluted with 0.1% aq $CF_3COOH$ and the grey precipitate containing mercury salts was removed by centrifugation and decantation. MALDI-TOF MS analysis of the supernatant indicated the presence of the peptide as a mercury adduct. More 2-mercaptoethanol (10 μL) was therefore added and the mixture was left to stand overnight. The mixture was then clarified as before, desalted by preparative RP-HPLC and lyophilised. The crude reduced (ascertained using the quantitative Ellman's test, refer G. L. Elmman (1959) Arch. Biochem. Biophys. 82, 70) material was used directly in the next step.

Oxidation was carried out as follows: The Acm-deprotected reduced material was dissolved in an aqueous buffered solution (0.1 M Tris acetate, pH 7.8; 5 mL) containing a mixture of oxidised (0.5 mM) and reduced (0.25 mM) glutathione. The reaction was followed by analytical RP-HPLC, which indicated rapid conversion. After 4 hours, the solution was lyophilised. The residue was redissolved in 0.1% aq $CF_3COOH$ and applied to an RP-HPLC column (Vydac 218TP1022, 2.2×25 cm). The column was developed at 5 mL/min with a gradient of 15 to 30% MeCN in 0.1% aq over 40 min). Appropriate peak fractions were pooled and lyophilised to afford pure title compound (0.30 mg). Analytical RP-HPLC: $t_R$=27.8 min (Vydac 218TP54, 0.46×25 cm, 1 mL/min, 15–30% MeCN in 0.1% aq $CF_3COOH$ over 40 min, λ=215 nm). MALDI-TOF MS: $[M+H]^+$=5089.9, $C_{211}H_{331}N_{65}O_{78}S_2$=5090.44. Amino acid analysis: Asx 5.24 (6), Thr 3.81(4), Ser 4.64(4), Glx 5.34(6), Gly 5.66(5), Cys 1.91(2), Ala 1.49(1), Val 2.33(2), Ile 0.71(1), Leu 3.56(3), Tyr 2.14(2), His 2.64(3), Lys 1.55(2), Arg 1.84(2), Abu 4.07(4).

EXAMPLE 5

Disulphide-cyclo [$Cys^{91}$–$Cys^{102}$,$Cys^{98}$–$Cys^{112}$, $Cys^{114}$–$Cys^{127}$]-[FVII $Glu^{82}$-$Thr^{128}$] [SEQ ID No. 1]

$Cys^{98,112}$(Acm) - [FVII $Glu^{82}$-$Thr^{128}$]: The peptidyl resin corresponding to the sequence [FVII $Glu^{82}$-$Thr^{128}$] was assembled in a similar fashion to the corresponding peptidyl resin of Example 1 with the exception that $Cys^{91}$, $Cys^{102}$, $Cys^{114}$ and $Cys^{127}$ were introduced as the Fmoc-Cys(Trt)-OH derivatives, whereas $Cys^{98}$ and $Cys^{112}$ were introduced as the Fmoc-Cys(Acm)-OH derivatives. The final peptidyl resin was cleaved and deprotected using the same procedures as in Example 1(4 hours reaction time). After $Et_2O$ precipitation and drying, the crude material was redissolved in 0.1% aq $CF_3COOH$ and was lyophilised. The residue was chromatographed by RP-HPLC (Vydac 218TP1022, 2.2×25 cm) at 5 mL/min using gradient elution from 15 to 30% MeCN in 0.1% aq $CF_3COOH$ over 2 hours. Appropriate peak fractions were pooled and lyophilised to afford pure title compound. Analytical RP-HPLC: $t_R$=28.6 min (Vydac 218TP54, 0.46×25 cm, 1 mL/min, 15–30% MeCN in 0.1% aq $CF_3COOH$ over 40 min). ES-MS: [M]=5306.4, $C_{213}H_{335}N_{67}O_{80}S_6$=5306.81.

Disulphide-cyclo[Cys91–$Cys^{102}$, $Cys^{114}$–$Cys^{127}$]-$Cys^{98,112}$(Acm)-[FVII $Glu^{82}$-$Thr^{128}$]:$Cys^{98,112}$(Acm)-[FVII $Glu^{82}$- $Thr^{128}$] was oxidised at 4° C. with a peptide concentration of 0.1 mg/mL in a buffered aqueous solution (0.1 M Tris acetate, pH 7.8) containing a mixture of oxidised (0.50 mM) and reduced (0.25 mM) glutathione. The reaction was followed by analytical RP-HPLC, which indicated essentially complete conversion after 2 hours to the title compound ($t_R$26.3 min using the same condtions as for the precursor). The mixture was then lyophilised, redissolved in 0.1% aq $CF_3COOH$ (3 mL) and chromatographed by RP-HPLC analogously to the reduced precursor, with the exception that the gradient was developed over 40 min at a flow rate of 9 mL/min. Peak fractions containing pure title compound were pooled and lyophilised.

Disulphide-cyclo[$Cys^{91}$–$Cys^{102}$, $Cys^{98}$–$Cys^{112}$, $Cys^{114}$–$Cys^{127}$]-[FVII $Glu^{82}$-$Thrl^{128}$]: disulphide-cyclo [$Cys^{91}$–$Cys^{102}$, $Cys^{114}$–$Cys^{127}$]-$Cys^{98,112}$(Acm)-[FVII $Glu^{82}$-$Thr^{128}$] was dissolved in $H_2O$ (250 μL). MeOH (250 μL), anisole (2 μL), and AcOH (30 μL) were then added. To this solution cyanogen iodide (5 mg) was added and the reaction mixture was agitated overnight in the dark. RP-HPLC and MALDI-TOF MS analysis of the mixture indicated essentially complete conversion. RP-HPLC: $t_R$=13.8 min (starting material at 12.8 min) (Vydac 218TP54, 0.46×25 cm, 1 mL/min, 20–35% MeCN in 0.1% aq $CF_3COOH$ over 40 min). The reaction was then quenched by addition of excess 0.1 M aq $Na_2S_2O_3$ and was diluted to 2 mL with 0.1% aq $CF_3COOH$. This solution was purified by preparative RP-HPLC using the same conditions as for the precursor. Appropriate peak fractions containing the pure title compound were pooled and lyophilised. Analytical HP-HPLC $t_R$=27.2 min, purity 95% (Vydac 218TP54, 0.46× 25 cm, 1 mL/mim, 15–30% MeCN in 0.1% aq $CF_3COOH$ over 40 min, μ=215 nm) . MALI-TOF MS: $[M+H]^+$5159.6, $C_{207}H_{319}N_{65}O_{78}S_6$=5158.66. Amino acid analysis: Asx 5.81 (6), Thr 3.85(4), Ser 4.63(4), Glx 6.00(6), Gly 5.33(5), Cys 5.66(6), Ala 1.06(1), Val 2.15(2), Ile 1.03(1), Leu 2.93(3), Tyr 1.95(2), His 2.48(3), Lys 2.11(2), Arg 2.01(2).

EXAMPLE 6

Inhibition of factor VIIa/tissue factor-catalysed factor X activation by compounds of Examples 1 to 5

This was determined using a two-stage chromogenic biochemical in vitro assay, essentially as described (A. Kumar et al., 1991, *J. Biol. Chem,* 266, 915). In short: peptides were pre-incubated with lipidated TF (5 pM; from American Diagnostica, Inc., Greenwich, Conn., USA) and calcium (5 mM) for 10 min prior to addition of FVIIa (5 pM; from Novo Nordisk A/S, Gentofte, Denmark) and FX (20 nm: from Enzyme Research Laboratory, South Bend, Ind., USA). Reactions were terminated by addition of EDTA (50 mM) and formation of FXa was monitored using the chromogenic FXa substrate S2765 (0.4 mM; from Chromogenix, M öindal, Sweden) and measuring the absorbance increase at 405 nm in a microtitre plate reader. The concentration for half-maximal inhibition (IC50) was determined from dose-inhibition curves.

|  |  | $IC_{50}$ ($\mu M$) |
| --- | --- | --- |
| Example 1 | (fully linear) | 1.3 ± 0.7 (n = 16)[a] |
| Example 2 | ($Cys^{91}$–$Cys^{102}$) | 0.26 |
| Example 3 | ($Cys^{114}$–$Cys^{127}$) | 0.29 |
| Example 4 | ($Cys^{98}$–$Cys^{112}$) | 0.14 |
| Example 5 | (fully cyclic) | 0.08 |

[a]Value corrected for net peptide content. $IC_{50}$ value based on peptide weight was 3 $\mu M$.

We claim:

1. A peptide of the amino acid sequence of formula I

```
        82              85                      90
        Glu Thr His Lys Asp Asp Gln Leu Ile 95                      100
Cys Val Asn Glu Asn Gly Gly Cys Glu Gln 105                     110
Tyr Cys Ser Asp His Thr Gly Thr Lys Arg 115                     120
Ser Cys Arg Cys His Glu Gly Tyr Ser Leu 125             128
Leu Ala Asp Gly Val Ser Cys Thr (SEQ ID NO. 1)
``` of human factor VII and functional equivalents thereof in which amino acids in the region 82–90 and 113–182 are modified or absent; or the amino acids Ser, Thr, Ile, Leu, Lys, and Arg are each optionally modified by the substitutions Ser for The, Ile for Leu, and Lys for Arg and vice versa; or both, and optionally wherein at least one cysteine residue in the sequence of formula (I) is blocked or replaced and wherein cysteines which remain unblocked or unreplaced are present in a disulfide bonded state; or a salt or derivative of said peptide.

2. A peptide as claimed in claim 1 wherein one or more cysteine residues are replaced or blocked.

3. A peptide as claimed in claim 2 wherein the thio group of said cysteine residue is blocked by an optionally substituted $C_{1-5}$ alkyl or $C_{6-12}$ aralkyl group.

4. A peptide as claimed in claim 2 wherein said cysteine residue is replaced by glycine, alanine, serine or 2-aminobutyric acid.

5. A peptide as claimed in claim 2 wherein all six cysteine residues are replaced or blocked.

6. A peptide as claimed in claim 5 wherein the cysteine residues are replaced by 2-aminobutyric acid.

7. A peptide as claimed in claim 1 wherein the terminal amino group or the terminal carboxyl group or both terminal amino group and terminal carboxyl group are capped by an inert group.

8. A peptide as claimed in claim 7 wherein the terminal amino capping group is a $C_{1-5}$ alkanoyl group and wherein the terminal carboxyl capping group is a carbamoyl or ester group.

9. A peptide as claimed in claim 1 wherein any cysteine residue remaining unblocked or unreplaced is present in a natural half-cystine disulphide bonded state.

10. A pharmaceutical composition containing a peptide as claimed in claim 1 together with a pharmaceutically acceptable carrier.

11. A pharmaceutical composition as claimed in claim 10 in a form suitable for oral, nasal, parenteral or rectal administration.

12. A peptide as claimed in claim 1 for inhibition of blood coagulation.

13. A method of inhibiting blood coagulation in the mammalian body said method comprising administering to said body a peptide as claimed in claim 1.

```
GAG ACG CAC AAG GAT GAC CAG CTG ATC TGT GTG AAC GAG AAC  (SEQ ID NO 6)
GGC GGC TGT GAG CAG TAC TGC AGT GAC CAC ACG GGC ACC AAG
CGC TCC TGT CGG TGC CAC GAG GGG TAC TCT CTG CTG GCA GAC
GGG GTG TCC TGC ACA
```

14. A recombiant DNA molecule comprising an expression vector containing DNA according to the sequence:

and modifications thereof coding for the peptide as claimed in claim 1.

* * * * *